US008841084B2

(12) United States Patent
Liang et al.

(10) Patent No.: US 8,841,084 B2
(45) Date of Patent: Sep. 23, 2014

(54) METHODS FOR THE DETECTION AND MONITORING OF ACUTE MYOCARDIAL INFARCTION

(75) Inventors: Bruce T. Liang, Avon, CT (US); Heiko Schmitt, Farmington, CT (US); Michael Azrin, Southington, CT (US); Christopher C. Pickett, Farmington, CT (US); Allan S. Jaffe, Rochester, MN (US)

(73) Assignees: The University of Connecticut, Farmington, CT (US); Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/697,555

(22) PCT Filed: May 12, 2011

(86) PCT No.: PCT/US2011/036232
§ 371 (c)(1),
(2), (4) Date: Jan. 28, 2013

(87) PCT Pub. No.: WO2011/143412
PCT Pub. Date: Nov. 17, 2011

(65) Prior Publication Data
US 2013/0143232 A1 Jun. 6, 2013

Related U.S. Application Data (60) Provisional application No. 61/395,611, filed on May 14, 2010.

(51) Int. Cl.
*G01N 33/573* (2006.01)
*G01N 33/53* (2006.01)
*G01N 33/00* (2006.01)
*G01N 33/68* (2006.01)

(52) U.S. Cl.
CPC ........ *G01N 33/6893* (2013.01); *G01N 2800/52* (2013.01); *G01N 2800/324* (2013.01); *G01N 2800/50* (2013.01); *G01N 2333/96469* (2013.01); *G01N 2510/00* (2013.01)
USPC .............................. 435/7.4; 435/7.1; 435/7.92

(58) Field of Classification Search
CPC ........... C07K 14/4747; C07K 2317/73; C12Q 2600/118; G01N 2800/56; G01N 2510/00; G01N 2800/50
See application file for complete search history.

(56) References Cited

U.S. PATENT DOCUMENTS

| | | | |
|---|---|---|---|
| 5,485,277 A | 1/1996 | Foster | |
| 5,492,840 A | 2/1996 | Malmqvist et al. | |
| 5,567,301 A | 10/1996 | Stetter et al. | |
| 7,427,490 B2 * | 9/2008 | Valkirs et al. | ................. 435/7.92 |
| 7,745,150 B2 * | 6/2010 | Liang et al. | .................... 435/7.1 |
| 2007/0092911 A1 * | 4/2007 | Buechler et al. | ................ 435/7.1 |
| 2009/0226937 A1 | 9/2009 | Liang et al. | |

FOREIGN PATENT DOCUMENTS

WO 2009154818 A1 12/2009

OTHER PUBLICATIONS

Cowie et al. 2005. Br. J. Cardiol. 12:205-208.*
Hoekstra et al. 2002. 9:1146-1155.*
Agosto et al.; "Serum Caspase-3 p17 Fragment is Elevated in Patients With ST-Segment Elevation Myocardial Infarction"; Journal of the American College of Cardiology; 57(2); p. 220-p. 221; (2011).
Agosto et al., "Circulating Caspase-3 P17 Peptide Fragment in Patients with Heart Failure"; Journal of Cardial Failure; 15(6) p. S75; (2009); ISSN: 1071-9164 [retrieved on Jul. 30, 2009] Abstract 245; 1 page.
Gutpa et al.; "Cardiac Contractility Modulation Electrical Signals Normalized Expression of the Excitation-Contraction Coupling Proteins Presenillin-2 and Sorcin in Left Ventricular Myocardium of Dogs with Chronic Heart Failure"; Abstracts—Cardiac Function and Heart Failure; Journal of the American College of Cardiology; 51(10); pp. A35-A82; Abstract 1002-3; (2008).
International Search Report and Written Opinion; International Application No. PCT/US2011/036232; International Filing Date May 12, 2011; Applicant's File Reference UCT0178PCT; 16 pages.
Abbate et al.; "Infarct-Related Artery Occulusion, Tissue Markers of Ischaemia, and Increased Apoptosis in the Peri-Infarct Viable Myocardium"; European Heart Journal; 26; pp. 2039-2045; (2005).

* cited by examiner

*Primary Examiner* — Shulamith H Shafer
(74) *Attorney, Agent, or Firm* — Cantor Colburn LLP (57) ABSTRACT

Disclosed herein are methods of detecting and/or prognosing myocardial infarction by detecting a proteolytic fragment of caspase-3 such as the p17 fragment or the p12 fragment. The myocardial infarction can be STEMI or NSTEMI.

7 Claims, 2 Drawing Sheets

N=53, P=0.0004 vs. post MI, Wilcoxon Rank Sum test

SEQUENCE LISTING

```
<160> NUMBER OF SEQ ID NOS: 3

<210> SEQ ID NO 1
<211> LENGTH: 277
<212> TYPE: PRT
<213> ORGANISM: Homo sapiens

<400> SEQUENCE: 1

Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
            20                  25                  30

Leu Asp Asn Ser Tyr Lys Met Asp Tyr Pro Glu Met Gly Leu Cys Ile
        35                  40                  45

Ile Ile Asn Asn Lys Asn Phe His Lys Ser Thr Gly Met Thr Ser Arg
    50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95
```

-continued

Val Glu Leu Met Arg Asp Val Ser Lys Glu Asp His Ser Lys Arg Ser
            100                 105                 110

Ser Phe Val Cys Val Leu Leu Ser His Gly Glu Glu Gly Ile Ile Phe
        115                 120                 125

Gly Thr Asn Gly Pro Val Asp Leu Lys Lys Ile Thr Asn Phe Phe Arg
    130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Asp Asp Met Ala Cys His Lys Ile Pro Val Glu Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
    210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
            260                 265                 270

Leu Tyr Phe Tyr His
        275

<210> SEQ ID NO 2
<211> LENGTH: 147
<212> TYPE: PRT
<213> ORGANISM: Homo sapiens

<400> SEQUENCE: 2

Ser Gly Ile Ser Leu Asp Asn Ser Tyr Lys Met Asp Tyr Pro Glu Met
1               5                   10                  15

Gly Leu Cys Ile Ile Ile Asn Asn Lys Asn Phe His Lys Ser Thr Gly
            20                  25                  30

Met Thr Ser Arg Ser Gly Thr Asp Val Asp Ala Ala Asn Leu Arg Glu
        35                  40                  45

Thr Phe Arg Asn Leu Lys Tyr Glu Val Arg Asn Lys Asn Asp Leu Thr
    50                  55                  60

Arg Glu Glu Ile Val Glu Leu Met Arg Asp Val Ser Lys Glu Asp His
65                  70                  75                  80

Ser Lys Arg Ser Ser Phe Val Cys Val Leu Leu Ser His Gly Glu Glu
                85                  90                  95

Gly Ile Ile Phe Gly Thr Asn Gly Pro Val Asp Leu Lys Lys Ile Thr
            100                 105                 110

Asn Phe Phe Arg Gly Asp Arg Cys Arg Ser Leu Thr Gly Lys Pro Lys
        115                 120                 125

Leu Phe Ile Ile Gln Ala Cys Arg Gly Thr Glu Leu Asp Cys Gly Ile
    130                 135                 140

Glu Thr Asp
145

<210> SEQ ID NO 3
<211> LENGTH: 102
<212> TYPE: PRT
<213> ORGANISM: Homo sapiens

```
-continued

<400> SEQUENCE: 3

Ser Gly Val Asp Asp Met Ala Cys His Lys Ile Pro Val Glu Ala
1               5                   10                  15

Asp Phe Leu Tyr Ala Tyr Ser Thr Ala Pro Gly Tyr Tyr Ser Trp Arg
                20                  25                  30

Asn Ser Lys Asp Gly Ser Trp Phe Ile Gln Ser Leu Cys Ala Met Leu
            35              40                  45

Lys Gln Tyr Ala Asp Lys Leu Glu Phe Met His Ile Leu Thr Arg Val
        50              55                  60

Asn Arg Lys Val Ala Thr Glu Phe Glu Ser Phe Ser Phe Asp Ala Thr
65                  70                  75                  80

Phe His Ala Lys Lys Gln Ile Pro Cys Ile Val Ser Met Leu Thr Lys
                85                  90                  95

Glu Leu Tyr Phe Tyr His
                100
```

METHODS FOR THE DETECTION AND MONITORING OF ACUTE MYOCARDIAL INFARCTION

CROSS-REFERENCE TO RELATED APPLICATIONS

This application is a 371 of PCT/US2011/036232, filed May 12, 2011, which claims the benefit of priority to U.S. Patent Application Ser. No. 61/395,611 filed on May 14, 2010, under provisions of 35 U.S.C. 119 and the International Convention for the Protection of Industrial Property, which are incorporated by reference herein in their entirety.

STATEMENT REGARDING FEDERALLY SPONSORED RESEARCH & DEVELOPMENT

This invention was made with support from the United States Government under Grant Number HL48225. The U.S. Government has certain rights in the invention.

FIELD OF THE DISCLOSURE

The present disclosure is in the field of methods for the detection of cardiovascular conditions and diseases, and more specifically, in the field of methods for the detection of acute myocardial infarction.

BACKGROUND

Each year over a million people in the U.S. have a heart attack, also known as a myocardial infarction. About half of them die as a result. Many people have permanent heart damage or die because they don't get help immediately. The symptoms of a heart attack include chest discomfort such as pressure, squeezing, or pain; shortness of breath; discomfort in the upper body including the arms, shoulders, neck, and back; nausea; vomiting; dizziness; lightheadedness; and sweating. Most heart attacks happen when a clot in the coronary artery blocks the supply of blood and oxygen to the heart. Often this leads to an irregular heartbeat, called an arrhythmia, that causes a severe decrease in the pumping function of the heart. A blockage that is not treated within a few hours causes the affected heart muscle to die.

Acute myocardial infarction (AMI) is the death or necrosis of myocardial cells, caused by the interruption of the blood supply to the heart. Much of the damage associated with AMI is due to contraction band necrosis. However, it is now recognized that both apoptosis and necrosis contribute to the myocardial damage seen in patients with AMI with apoptosis contributing to up to 50% of the overall injury. In patients who die after AMI, apoptosis is present in both regions adjacent to and remote from the infarction. Further, while timely reperfusion of the ischemic myocardium can limit infarct size, reperfusion itself may cause damage to the previously ischemic myocardium, including augmentation of the apoptosis which occurs during occlusion. The number of apoptotic cells in the perinecrotic myocardium progressively increases during reperfusion, contributing substantially to the overall extent of the infarction.

Cardiac biomarkers have revolutionized the care of cardiovascular patients in numerous arenas, including prediction and detection of pre-clinical disease, improved detection of cardiac injury including non-ST-segment-elevation myocardial infarction (NSTEMI), prognostication in both acute and chronic disease presentations, and monitoring the response to treatment. Most biomarkers, however, are markers of necrosis. There remains a need for new biomarkers, specifically a biomarker that can detect and quantify apoptosis, suitable detecting and/or diagnosing acute myocardial infarction.

SUMMARY

In one embodiment, a method for detecting the presence of apoptosis in acute myocardial infarction in an individual suspected of having had a myocardial infarction, comprises directly or indirectly measuring a level of a caspase-3 proteolytic fragment in at least two blood samples taken within a 24 hour period from the individual suspected of having had a myocardial infarction, wherein the caspase-3 proteolytic fragment is a p17 or p12 fragment, and detecting the presence of apoptosis in acute myocardial infarction in the individual when the level of the caspase-3 proteolytic fragment is greater in the first blood sample compared to the last blood sample taken within the 24 hour period, and when the level of the caspase-3 proteolytic fragment in the first and last blood samples is at least 20% greater than the level of the capsase-3 proteolytic fragment in a healthy control sample.

In another embodiment, a prognostic method for determining a likelihood of a future myocardial infarction or heart failure in an individual diagnosed as having had a myocardial infarction comprises directly or indirectly measuring a peak acute myocardial infarction level of a caspase-3 proteolytic fragment in a blood sample taken from the individual during the acute phase of myocardial infarction, directly or indirectly identifying a post-myocardial infarction level of the caspase-3 proteolytic fragment in a blood sample taken at least one week post-myocardial infarction, comparing the peak acute myocardial infarction level and the post-myocardial infarction level of the caspase-3 proteolytic fragment to a control level of the caspase-3 proteolytic fragment, and predicting the likelihood of future myocardial infarction, left ventricular dysfunction, death, or heart failure in the individual diagnosed as having had a myocardial infarction based on the comparison of the peak acute myocardial infarction level, the post-myocardial infarction level, and the control level of the caspase-3 proteolytic fragment.

In yet another embodiment, a method for monitoring a response to post-myocardial infarction therapy in an individual diagnosed as having had a myocardial infarction, comprising directly or indirectly measuring a peak acute myocardial infarction level of a caspase-3 proteolytic fragment in a blood sample taken from the individual during the acute phase of myocardial infarction, directly or indirectly identifying a post-myocardial infarction level of the caspase-3 proteolytic fragment in a blood sample taken at least one week post-myocardial infarction, administering post-myocardial infarction therapy to the individual and measuring the post-therapy level of the caspase-3 proteolytic fragment, and monitoring the response to post-myocardial infarction therapy by comparing the peak acute myocardial infarction level, the post-myocardial infarction level, and the post-therapy levels of the caspase-3 proteolytic fragment.

DETAILED DESCRIPTION

Disclosed herein are new methods to detect the presence of apoptosis during acute myocardial infarction (AMI) in patients. The methods use a simple blood test to quantify the amount of a peptide that is released into the circulation when a subject is experiencing an AMI. In such a clinical situation, it is likely that most of the signal that is produced, i.e., most of the peptide released into the circulation will originate from the heart. The present inventors have demonstrated for the first time that the measured levels of the peptide rise during the acute phase of MI, and then drop during the post-acute period, although not necessary to control levels. Thus, the peptide levels can be used to confirm that an individual, for example an individual admitted to an emergency room, has had a myocardial infarction. Since only approximately 10% of those who present to emergency rooms with symptoms turn out to have a real myocardial infarction, having a blood test for a marker that has a negative predictive value would be extremely helpful to clinicians. Further, since in the post-acute period the serum p17 peptide level remains higher than that in healthy control subjects, it is possible that there is residual ongoing apoptosis even after the acute MI. The levels of peptide during the acute and post-myocardial infarction period can also be used to prognosticate future outcomes for the patient and to assess the efficacy of post-myocardial infarction treatment.

In the specific studies described herein, an enzyme-linked immunoassay was used to determine the serum level of a cleaved p17 fragment (p17) of caspase-3, the end effector caspase for apoptosis, in patients with ST-segment-elevation myocardial infarction (STEMI). The hypothesis that serum p17 levels are increased during AMI was tested, and the association of peak serum p17 level with peak levels of cardiac Troponin I (cTnI), CK-MB, and CK was also determined. These goals were facilitated by the fact that reperfusion of the infarct-related artery by primary percutaneous coronary intervention (PCI) was successfully accomplished in all of these patients. The measurement of p17 peptide in these patients is likely due at least in part if not entirely to release of p17 peptide from apoptotic cardiac myocytes. The inventors herein have unexpectedly discovered that cleaved caspase-3 products can be quantified in human serum and that they are elevated shortly after myocardial infarction, and particularly after reperfusion therapy.

The terms "myocardial infarction" and "heart attack" are used herein as having very similar meanings, i.e., the same meanings used by those skilled in the general medical and cardiology fields. As used herein myocardial infarction and heart attack are both clinical conditions that are distinctly different from congestive heart failure. Congestive heart failure is a generally a chronic, long-term condition in which the heart can no longer pump enough blood to the rest of the body. The symptoms of congestive heart failure generally appear slowly, in contrast to a myocardial infarction, the symptoms of which generally create a medical emergency.

Myocardial infarction can be classified into two types based on the patient's ECG, ST-segment elevation MI (STEMI) and non-ST-segment elevation MI (NSTEMI). Myocardial infarctions or heart attacks occur when a coronary artery becomes occluded by a blood clot, causing at least some of the heart muscle supplied by the artery to become infarcted, that is, to die. In STEMI, the coronary artery is completely blocked by the blood clot, thus virtually all of the heart muscle supplied by the affected artery becomes infarcted. In this more severe form of heart attack, the ECG shows a characteristic elevation in the "ST segment." In NSTEMI, the blood clot only partially occludes the artery, thus only a portion of the heart muscle supplied by the artery becomes infarcted. NSTEMI does not produce a characteristic elevation in the "ST segment" of the ECG because the artery is only partially blocked.

In one embodiment, an individual suspected of having a myocardial infarction is admitted to an emergency room upon having symptoms of a myocardial infarction. Approximately 80% to 90% of individuals admitted for a suspected myocardial infarction, however, have not had a myocardial infarction. By performing the method described herein on a patient within the first few hours of the suspected myocardial infarction, the physician can confirm or rule out myocardial infarction as a source of the individual's symptoms. In a specific embodiment, the individual is admitted for primary percutaneous coronary intervention (PCI), that is, percutaneous coronary intervention performed in an emergency situation. Percutaneous coronary intervention includes angioplasty and also includes techniques used to widen a narrowed artery thus allowing blood to flow through.

As used herein, the term blood sample includes whole blood samples as well as serum and plasma samples. Blood plasma is the liquid component of blood in which the blood cells are suspended. Blood serum is blood plasma without fibrinogen and other clotting factors.

Caspase-3 (SEQ ID NO:1) is synthesized as an inactive proenzyme (32 kDa) that is processed in cells undergoing apoptosis by self-proteolysis and/or cleavage by another upstream protease. The processed form of caspase-3 consists of large (17 kDa; p17 fragment) (SEQ ID NO:2) and small (12 kDa; p12 fragment) (SEQ ID NO:3) subunits which associate to form an active enzyme. Disclosed herein are methods of detecting and/or prognosing myocardial infarction by detecting a proteolytic fragment of caspase-3 such as the p17 peptide or the p12 fragment.

There are robust experimental data demonstrating the importance of apoptosis during AMI. However, the ability to measure and detect apoptosis clinically has made it difficult to document a role in patients. The data presented herein for the first time demonstrate increases in the apoptosis marker caspase-3 p17 peptide during STEMI. There was an association of p17 with known biomarkers of cardiac injury in keeping with the concept that both measures may reflect infarct size. However, the correlations were not tight because cardiac troponin measures both necrosis and apoptosis while caspase-3 p17 level measures apoptosis only. In fact, the relative contribution of necrosis and apoptosis to infarction depends on the time after coronary artery occlusion. Apoptosis is a major form of damage after occlusion whereas necrosis occurs after apoptosis and contributes to progressive myocyte loss with time.

In the setting of acute MI, both ischemia from coronary occlusion and reperfusion contribute to the myocardial damage that occurs during acute MI. In patients who die from the episode and in those who survive the acute event but develop congestive heart failure, apoptosis is present and very likely plays an important role by augmenting the extent of myocyte injury. The increased stretch from the bulging of the necrotic area during systolic contraction and abnormal diastolic overload also can cause apoptotic cell death in regions adjacent to and remote from the infarcted area. Some of this appears to be related to a calpain mediated mechanism. However, evidence for apoptosis of cardiac myocytes during the acute phase of MI in humans has heretofore been lacking. The present study used a serum assay for p17 peptide of caspase-3 to detect apoptosis. Values may have been increased even prior to reperfusion, however values were obtained after the acute intervention so as not to interfere with the need for urgent and prompt intervention in these STEMI patients. Nonetheless, even if produced prior to reperfusion, successful reperfusion may set the stage for release of this small peptide from the apoptotic myocardium.

The assay applied herein for measuring the caspase-3 p17 peptide in human serum should in principle have high specificity for the apoptotic process. We hypothesized that due to its small size, p17 peptide would escape into circulation from cells and thus become detectable. That apoptotic human HeLa cells can release p17 peptide into extracellular medium provides support for this hypothesis. The circulating p17 level was determined to test this hypothesis in patients with acute MI. This hypothesis is supported by the following lines of evidence. First, serum p17 peptide was elevated during acute STEMI. The p17 peptide level fell after infarction. The fall of p17 peptide level after the acute phase of infarct is similar to that of known biomarkers of MI. Second, the peak p17 peptide level was significantly correlated with the peak cTnI level during the acute phase of the infarct. Since cardiac cTnI is selective for cardiac rather than skeletal muscles, the significant correlation between the two levels suggests that the serum p17 peptide likely came from the damaged cardiac myocytes during acute STEMI. Third, there was also a significant correlation between peak p17 peptide level and peak CK-MB level. Although CK-MB can also be derived from skeletal muscles, its concentration is much lower in skeletal than in cardiac muscles. The release of CK-MB with a typical rise and fall pattern during the acute infarction makes it very likely that the MB fraction came from the damaged myocardium. The correlation with peak CK-MB is also supportive of concept that the serum p17 peptide was derived from the infarcting myocardium. Cardiac cTnI level obtained 24 hrs after the infarct is significantly correlated with the infarct size determined by cardiac magnetic resonance imaging. Since activated cleaved caspase-3 is primarily selective for apoptotic cardiac myocytes and since serum cTnI is increased in both necrotic and apoptotic myocyte death, correlation of serum p17 peptide level with cTnI provide validation for the concept that serum p17 peptide level can reflect cardiac myocyte apoptosis.

In one embodiment, a method for detecting the presence of apoptosis in acute myocardial infarction in an individual suspected of having had a myocardial infarction comprises directly or indirectly measuring a level of a caspase-3 proteolytic fragment in at least two blood samples taken within a 24 hour period from the individual suspected of having had a myocardial infarction, wherein the caspase-3 proteolytic fragment is a p17 or p12 fragment, and detecting a myocardial infarction in the individual when the level of the caspase-3 proteolytic fragment has risen by any extent would indicate apoptotic cell death in the heart. In specific embodiments, if the level is at least 10% greater in the first blood sample compared to the last blood sample taken within the 24 hour period, and/or when the level of the caspase-3 proteolytic fragment in the first and last blood samples is at least 20% greater than the level of the capsase-3 proteolytic fragment in a sample obtained from a healthy control subject, a myocardial infarction is detected. In one embodiment, the level of the caspase-3 proteolytic fragment is at least 10% greater, specifically 15% greater, and more specifically 20% greater in the first blood sample compared to the last blood sample taken within the 24 hour period. In another embodiment, the level of the caspase-3 proteolytic fragment in the first and last blood samples is at least 20% greater, specifically 25% greater, and more specifically 30% greater than the level of the capsase-3 proteolytic fragment in a control sample from healthy subjects.

In one embodiment, the control sample is from a normal population, or from the individual when the individual is not in the acute myocardial infarction or near-myocardial infarction state.

In one embodiment, the individual has been admitted to an emergency room for a suspected myocardial infarction. In another embodiment, the individual has been admitted to the emergency room for primary percutaneous coronary intervention. The myocardial infarction may be STEMI or NSTEMI, specifically STEMI. While the caspase-3 marker rises after AMI, the levels can increase even more after reperfusion therapy. Thus, if reperfusion therapy is performed, it is advantageous to analyze a blood sample taken after reperfusion therapy for the levels of caspase-3 proteolytic fragment.

In one embodiment, at least one blood sample is taken after reperfusion therapy. In general, patients that present with suspected AMI are treated with immediate reperfusion, generally thrombolytic therapy or PCI.

It has been unexpectedly found by the inventors herein that the levels of caspase-3 proteolytic fragment in blood samples rises in the acute phase of myocardial infarction, generally within the first 24 hours of a myocardial infarction, and then gradually decrease. Thus, unlike the previous observations with congestive heart failure, there is a time-dependence to the observed levels of caspase-3 proteolytic fragment in acute myocardial infarction. In the case of congestive heart failure, the caspase-3 proteolytic fragment levels remain relatively constantly higher than a control population over the course of weeks and even months. In the case of acute myocardial infarction, the proteolytic fragment levels rise to much higher levels than the congestive heart failure levels in the acute myocardial infarction phase, and then gradually decrease, although generally not to control population levels. Thus, in the case of myocardial infarction, one is looking for a sharp increase in proteolytic fragment levels, followed by a slight (about 10 or 15%) decrease within the first 24 hours. The pattern, extent, and time course of the rise in serum p17 levels is different from those in heart failure.

Without being held to theory, it is believed that the peak caspase-3 p17 level is correlated with the amount of cardiac apoptosis. That is, the higher the peak caspase-3 p17 level, the greater the amount of cardiac apoptosis. Until the studies whose results are shown herein, there was no other method to detect apoptosis via a blood sample or to monitor the extent of apoptosis in the heart.

In a specific embodiment, the method includes directly or indirectly measuring a level of the caspase-3 proteolytic fragment in a total of four blood samples taken eight hours apart over a 24 hour period.

The method can further include identifying a peak acute myocardial infarction level of the caspase-3 proteolytic fragment in the individual. Identification of the peak acute-MI level can be an indication of the severity of the MI and can also be used to prognosticate for a future event such as a future MI or heart failure. In this regard, it may be advantageous to directly or indirectly identify a post-myocardial infarction level of caspase-3 proteolytic fragment in a blood sample taken at least one week post-myocardial infarction. Post-myocardial infarction, the levels of caspase-3 proteolytic fragment tend to remain elevated compared to control levels. The peak level and post-myocardial infarction level of the caspase-3 fragment are prognostic for a future myocardial infarction, heart failure, left ventricular dysfunction heart failure or death.

In another embodiment, a prognostic method for determining a likelihood of a future myocardial infarction or heart failure in an individual diagnosed as having had a myocardial infarction, comprises directly or indirectly measuring a peak acute myocardial infarction level of a caspase-3 proteolytic fragment in a blood sample taken from the individual during the acute phase of myocardial infarction, directly or indirectly identifying a post-myocardial infarction level of the caspase-3 proteolytic fragment in a blood sample taken at least one week post-myocardial infarction, comparing the peak acute myocardial infarction level and the post-myocardial infarction level of the caspase-3 proteolytic fragment to a control level of the caspase-3 proteolytic fragment, and predicting the likelihood of future myocardial infarction or heart failure in the individual diagnosed as having had a myocardial infarction based on the comparison of the peak acute myocardial infarction level, the post-myocardial infarction level, and the control level of the caspase-3 proteolytic fragment.

The peak acute MI level, the post-MI level, or the difference between the peak or the post-MI level and that of the healthy control level may be associated with ongoing cardiac apoptosis, recurrent MI, development of left ventricular systolic dysfunction as measured by left ventricular ejection fraction, development of heart failure including ischemic heart failure, or death.

In another embodiment, a method for monitoring a response to post-myocardial infarction therapy in an individual diagnosed as having had a myocardial infarction, comprises directly or indirectly measuring a peak acute myocardial infarction level of a caspase-3 proteolytic fragment in a blood sample taken from the individual during the acute phase of myocardial infarction, directly or indirectly identifying a post-myocardial infarction level of the caspase-3 proteolytic fragment in a blood sample taken at least one week post-myocardial infarction, administering post-myocardial infarction therapy to the individual and measuring the a post-therapy level of the caspase-3 proteolytic fragment, and monitoring the response to post-myocardial infarction therapy by comparing the peak acute myocardial infarction level, the post-myocardial infarction level, and the post-therapy levels of the caspase-3 proteolytic fragment.

In one embodiment, a decrease in peak acute MI capsase-3 proteolytic fragment level or a decrease in post-MI level at 3 months after therapies for acute MI patients would suggest the efficacy of MI treatment. For example, serial determination of p17 levels after acute MI and quantifying the area under the p17 curve should be highly predictive of therapeutic efficacy. Further, the decreases in such p17 levels should be correlated with a higher left ventricular ejection fraction, a lower incidence of developing heart failure or recurrent MI or death. Examples of therapies include prompt door-to-balloon time (with a goal of less than 90 min) by PCI or lytics therapy, institution of appropriate dosages of beta blockers, of angiotension converting enzyme inhibitors or angiotensin receptor blockers, of aspirin and/or Plavix®, and of an appropriate dosage of a statin drug.

Caspases are a family of cysteine acid proteases that are essential to the intracellular processes leading to apoptosis. Pro-apoptotic signals trigger the activation of the initiator caspases (such as caspase-8, -9, -10), which cleave and in turn activate the downstream effector caspases. Among the effector caspases, caspase-3 is considered to be the key executioner in the apoptotic pathway. It is activated by cleavage of its inactive zymogen into active p17 and p12 fragments. The cleaved p17 fragment can be detected with a commercial sandwich ELISA assay. The human caspase-3 has accession number NP_116786.

Caspase-3 (SEQ ID NO:1) has the sequence:

```
  1  mentensvds ksiknlepki ihgsesmdsg isldnsykmd ypemglciii nnknfhkstg
 61  mtsrsgtdvd aanlretfrn lkyevrnknd ltreeivelm rdvskedhsk rssfvcvlls
121  hgeegiifgt ngpvdlkkit nffrgdrcrs ltgkpklfii qacrgteldc gietdsgvdd
181  dmachkipve adflyaysta pgyyswrnsk dgswfiqslc amlkqyadkl efmhiltrvn
241  rkvatefesf sfdatfhakk qipcivsmlt kelyfyh
```

The p17 fragment is amino acids 29-175 (SEQ ID NO:2), and has the sequence:

```
sgisldnsyk mdypemglci iinnknfhks tgmtsrsgtd vdaanlretf rnlkyevrnk ndltreeive lmrdvskedh skrssfvcvl lshgeegiif gtngpvdlkk itnffrgdrc rsltgkpklf iiqacrgtel dcgietd
```

The p12 fragment is amino acids 176-277 (SEQ ID NO: 3) and has the sequence:

```
sgvdd dmachkipve adflyaysta pgyyswrnsk dgswfiqslc amlkqyadkl efmhiltrvn rkvatefesf sfdatfhakk qipcivsmft kelyfyh
```

The term "level" relates to amount or concentration of a peptide or polypeptide in a patient or a sample taken from a patient. The term "measuring" accordingly relates to determining the amount or concentration, preferably semi-quantitatively or quantitatively, of the nucleic acid, peptide, polypeptide, or other substance of interest. Measuring can be done directly or indirectly. Indirect measuring includes measuring of cellular responses, bound ligands, labels, or enzymatic reaction products. In one embodiment, indirect measuring includes the use of an antibody.

The amount, level or presence of a caspase-3 proteolytic fragment is determined using any of a variety of techniques known to the skilled artisan such as, for example, a technique selected from the group consisting of, immunohistochemistry, immunofluorescence, an immunoblot, a Western blot, a dot blot, an enzyme linked immunosorbent assay (ELISA), radioimmunoassay (RIA), enzyme immunoassay, fluorescence resonance energy transfer (FRET), matrix-assisted laser desorption/ionization time of flight (MALDI-TOF), electrospray ionization (ESI), mass spectrometry (including tandem mass spectrometry, e.g. LC MS/MS), surface-enhanced laser desorption ionization mass spectrometry (SELDI-MS), biosensor technology, evanescent fiber-optics technology or protein chip technology.

In one embodiment, the assay used to determine the amount or level of caspase-3 or a fragment thereof is a semi-quantitative assay. In another embodiment, the assay used to determine the amount or level of caspase-3 or a fragment thereof is a quantitative assay. As will be apparent from the preceding description, such an assay may require the use of a suitable control, e.g., from a normal individual or matched normal control.

Standard solid-phase ELISA or FLISA formats are particularly useful in determining the concentration of a protein from a variety of samples.

Caspase-3 or a fragment thereof can be measured in the body fluid sample, e.g., serum or plasma, using assays that detect caspase-3 or a fragment thereof, for example, radioisotopic immunoassays or non-isotopic immunoassays, e.g., fluorescent immunoassays, enzymatic immunoassays, such as an enzyme linked immunoassay (ELISA).

By way of example, other means for determining and measuring caspase-3 or a fragment thereof in a sample include affinity chromatography, ligand binding assays, and lectin binding assays. Immunoassays, especially non-radioisotopic immunoassays, are particularly suitable. Normal range and normal mean values can be determined for the assay being carried out based on normal (healthy) population samples, as is known and practiced in the art.

As used herein, the term antibody includes polyclonal and monoclonal antibodies of any isotype (IgA, IgG, IgE, IgD, IgM), or an antigen-binding portion thereof, including but not limited to F(ab) and Fv fragments, single chain antibodies, chimeric antibodies, humanized antibodies, and a Fab expression library. Antibodies useful as detector and capture antibodies may be prepared by standard techniques well known in the art.

Antibodies generated against caspase-3 or a fragment thereof, can be obtained by direct injection of an immunogenic caspase-3 preparation into an animal, or by administering all, or the caspase-3 p-17 polypeptides to an animal, preferably a nonhuman animal. For the preparation of monoclonal antibodies, a suitable technique which provides antibodies produced by continuous cell line cultures can be used. Examples include the hybridoma technique, the trioma technique, the human B-cell hybridoma technique, and the EBV-hybridoma technique to produce human monoclonal antibodies. Techniques described for the production of single chain antibodies can be adapted to produce single chain antibodies to caspase-3. Also, transgenic mice may be used to express humanized antibodies to immunogenic caspase-3 or a fragment thereof.

Methods for producing and screening for antibodies to caspase-3 or a fragment thereof using hybridoma technology are routine and well known in the art. In a nonlimiting example, mice can be immunized with an immunogen, caspase-3 or a fragment thereof, or with a cell expressing these polypeptides or peptides. Once an immune response is detected, e.g., antibodies specific for the antigen are detected in the sera of immunized mice, the spleen is harvested and splenocytes are isolated. The splenocytes are then fused by well-known techniques to any suitable myeloma cells available from the ATCC. Hybridomas are selected and cloned by limiting dilution techniques. The hybridoma clones are then assayed by methods known in the art to determine and select those cells that secrete antibodies capable of binding to caspase-3 or a fragment thereof. Ascites fluid, which generally contains high levels of antibodies, can be generated by injecting mice with positive hybridoma clones.

Caspase-3 or a fragment thereof comprising one or more immunogenic caspase-3 epitopes which elicit an antibody response can be introduced together with a carrier protein, such as an albumin, to a host animal (such as rabbit, mouse, rat, sheep, or goat). Alternatively, if the polypeptide is of sufficient length (e.g., at least about 25 amino acids), the polypeptide can be presented without a carrier. However, immunogenic epitopes comprising as few as 5 to 10 amino acids have been shown to be sufficient to raise antibodies capable of binding to, at the very least, linear epitopes in a denatured polypeptide (e.g., in Western blotting).

Caspase-3 or a fragment thereof can be used to induce antibodies according to methods well known in the art including, but not limited to, in vivo immunization, in vitro immunization, and phage display methods. If in vivo immunization is used, animals can be immunized with free peptide; however, the anti-peptide antibody titer may be boosted by coupling the peptide to a macromolecular carrier, such as keyhole limpet hemacyanin (KLH), or tetanus toxoid (TT). For instance, peptides containing cysteine residues can be coupled to a carrier using a linker such as maleimidobenzoyl-N-hydroxysuccinimide ester (MBS), while other peptides may be coupled to carriers using a more general linking agent, such as glutaraldehyde.

Antibodies specific for caspase-3 or a fragment thereof are produced by methods known in the art for the synthesis of antibodies, in particular, by chemical synthesis, by intracellular immunization (i.e., intrabody technology), or by recombinant expression techniques. Methods of producing antibodies include, but are not limited to, hybridoma technology, EBV transformation, as well as through the use recombinant DNA technology. Recombinant expression of an antibody, or a fragment, derivative, variant or analog thereof, (e.g., a heavy or light chain of an anti-caspase-3 antibody), requires construction of an expression vector containing a polynucleotide that encodes the antibody. Once a polynucleotide encoding an antibody molecule or a heavy or light chain of an antibody, or portion thereof (preferably containing the heavy or light chain variable domain) has been obtained, the vector for the production of the antibody molecule can be produced by recombinant DNA technology using techniques well known in the art. In vitro recombinant DNA techniques, synthetic techniques, and in vivo genetic recombination methods, which are well known to those skilled in the art, can be used to construct expression vectors containing antibody coding sequences and appropriate transcriptional and translational control signals. Such vectors can include the nucleotide sequence encoding the constant region of the antibody molecule and the variable region of the antibody cloned into such a vector for expression of the entire heavy or light chain.

The expression vector is then introduced into a host cell by conventional techniques and the transfected cells are cultured by conventional techniques to produce an anti-capsase-3 antibody. A variety of host expression vector systems can be utilized to express the antibody molecules. Such expression systems represent vehicles by which the coding sequences of interest can be expressed, their encoded products produced and subsequently purified. These systems also represent cells which can, when transformed or transfected with the appropriate nucleotide coding sequences, express an antibody molecule of the invention in situ. Cell expression systems include, but are not limited, to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces* or *Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus (CaMV) or tobacco mosaic virus (TMV)), transformed with recombinant plasmid expression vectors (e.g., Ti plasmid) containing antibody coding sequences; or mammalian cell systems (e.g., COS, CHO, BHK, 293, 3T3, NSO cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Specifically, bacterial cells such as *E. coli*, and more specifically, eukaryotic cells, especially for the expression of whole recombinant antibody molecules, are used for the expression of a recombinant antibody molecule. For example, mammalian cells such as Chinese hamster ovary (CHO) cells, in conjunction with a vector such as the major intermediate early gene promoter element from human cytomegalovirus, is an effective expression system for antibody production.

Once an anti-caspase-3 antibody has been produced by an animal, chemically synthesized, or recombinantly expressed, it can be purified by methods known in the art for the purification of an immunoglobulin or polypeptide molecule, for example, by chromatography (e.g., ion exchange, affinity, particularly by affinity for the specific antigen, Protein A, and sizing column chromatography), centrifugation, differential solubility, or by any other standard technique for the purification of proteins.

In one embodiment, an ELISA assay initially involves preparing an antibody specific to caspase-3 or a fragment thereof, preferably a monoclonal antibody. In addition, a reporter antibody is used. In some ELISA protocols, the reporter antibody recognizes and binds to the caspase-3 specific monoclonal antibody. To the reporter antibody is attached a detectable reagent such as a radioactive isotope, a fluorescent moiety, a chemiluminescent moiety, or, in an ELISA, an enzyme, such as horseradish peroxidase or alkaline phosphatase.

As is appreciated by those skilled in the art, ELISAs can be performed in a number of assay formats. In one ELISA format, a host sample, e.g., a patient body fluid sample, is incubated on a solid support, e.g., the wells of a microtiter plate, or a polystyrene dish, to which the proteins in the sample can bind. Any free protein binding sites on the dish are then blocked by incubating with a non-specific protein such as bovine serum albumin. The monoclonal antibody is then added to the solid support, e.g., the wells or the dish, and allowed to incubate. During the incubation time, the monoclonal antibodies attach to any caspase-3 polypeptides that have attached to the polystyrene dish.

Unbound monoclonal antibody is washed away using an appropriate buffer solution. The reporter antibody, e.g., linked to horseradish peroxidase, is added to the support, thereby resulting in the binding of the reporter antibody to any monoclonal antibody which has bound to caspase-3 or a fragment thereof present in the sample. Unattached reporter antibody is then washed away. Peroxidase substrate is added to the support and the amount of color developed in a given time period provides a measurement of the amount of caspase-3 or a fragment thereof that is present in a given volume of patient sample when compared to a standard curve.

In another ELISA format, an antibody specific for a particular analyte is attached to the solid support, i.e., the wells of a microtiter plate or a polystyrene dish, and a sample containing analyte is added to the substrate. Detectable reporter antibodies, which bind to the analyte that has bound to the capture antibodies on the support, are then added, after the appropriate incubations and washings, and analyte-antibody complexes are detected and quantified.

In one embodiment, the ELISA assay is a sandwich type ELISA immunoassay typically performed using microtiter plates. A capture antibody, that can be polyclonal or monoclonal, preferably a monoclonal antibody, that specifically recognizes an epitope in the extracellular portion caspase-3 or a fragment thereof is used, along with a labeled detector antibody, e.g., an alkaline phosphatase-labeled antibody, or a horse radish peroxidase-labeled antibody, preferably a monoclonal antibody. The detector antibody also specifically recognizes an epitope on the extracellular protein domain of caspase-3 or a fragment thereof. Preferably, the capture antibody does not inhibit binding to caspase-3 or a fragment thereof. The production of both polyclonal and monoclonal antibodies, particularly monoclonal antibodies that are specific for caspase-3 or a fragment thereof, is performed using techniques known in the art.

In a particular embodiment, a capture anti-caspase-3 antibody of the assay method, is immobilized on the interior surface of the wells of the microtiter plate. To perform the assay, an appropriate volume of sample is incubated in the wells to allow binding of the antigen by the capture antibody. The immobilized antigen is then exposed to the labeled detector antibody. Addition of substrate to the wells, if the detectable label is alkaline phosphatase, for example, allows the catalysis of a chromogen, i.e., para-nitrophenylphosphate (pNPP), if the label is alkaline phosphatase, into a colored product. The intensity of the colored product is proportional to the amount of caspase-3 that is bound to the microtiter plate.

Standards are used to allow accurate quantitative determinations of caspase-3 or a fragment thereof in the samples undergoing analysis. A microtiter plate reader simultaneously measures the absorbance of the colored product in the standard and the sample wells. Correlating the absorbance values of samples with the standards run in parallel in the assay allows the determination of the levels of caspase-3 or a fragment thereof in the sample. Samples are assigned a quantitative value of caspase-3 or a fragment thereof in nanograms per milliliter (ng/ml) of serum, plasma, other body fluid, or cell culture fluid.

For ease and simplicity of detection, and its quantitative nature, an exemplary assay is the sandwich or double antibody assay of which a number of variations exist. In one embodiment of a sandwich assay, unlabeled antibody is immobilized on a solid phase, e.g., a microtiter plate, and the sample to be tested is added. After a certain period of incubation to allow formation of an antibody-antigen complex, a second antibody, labeled with a reporter molecule capable of inducing a detectable signal, is added and incubation is continued to allow sufficient time for binding with the antigen at a different site, resulting with a formation of a complex of antibody-antigen-labeled antibody. The presence of the antigen is determined by observation of a signal which may be quantitated by comparison with control samples containing known amounts of antigen.

Alternatively, the amount of caspase-3 or a fragment thereof is detected using a radioimmunoassay (RIA). The basic principle of the assay is the use of a radiolabeled antibody or antigen to detect antibody-antigen interactions. An antibody or ligand that specifically binds to a protein is bound to a solid support and a sample brought into direct contact with said antibody. To detect the level of bound antigen, an isolated and/or recombinant form of the antigen is radiolabeled and brought into contact with the same antibody. Following washing, the level of bound radioactivity is detected. As any antigen in the biological sample inhibits binding of the radiolabeled antigen the level of radioactivity detected is inversely proportional to the level of antigen in the sample. Such an assay may be quantitated by using a standard curve using increasing known concentrations of the isolated antigen.

In another embodiment, Western blotting is used to determine the level of caspase-3 or a fragment thereof in a sample. In such an assay protein from a sample is separated using sodium doedecyl sulphate polyacrylamide gel electrophoresis (SDS-PAGE) using techniques known in the art. Separated proteins are then transferred to a solid support, such as, for example, a membrane (e.g., a PVDF membrane), using, for example, electrotransfer. This membrane is then blocked and probed with a labeled antibody or ligand that specifically binds to caspase-3 or a fragment thereof. Alternatively, a labeled secondary, or even tertiary, antibody or ligand is used to detect the binding of a specific primary antibody. The level of label is then determined using an assay appropriate for the label used.

In other embodiments, the detection of the level of caspase-3 or a fragment thereof is done by a method such as, for example, mass spectrometry, matrix-assisted laser desorption/ionization time of flight (MALDI-TOF), electrospray ionisation (ESI), protein chip, biosensor technology, or fluorescence resonance energy transfer.

Biosensor devices generally employ an electrode surface in combination with current or impedance measuring elements to be integrated into a device in combination with the assay substrate (such as that described in U.S. Pat. No. 5,567,301). An antibody/ligand that specifically binds to a protein of interest is preferably incorporated onto the surface of a biosensor device and a biological sample contacted to said device. A change in the detected current or impedance by the biosensor device indicates protein binding to said antibody. Some forms of biosensors known in the art also rely on surface plasmon resonance to detect protein interactions, whereby a change in the surface plasmon resonance surface of reflection is indicative of a protein binding to a ligand or antibody (U.S. Pat. Nos. 5,485,277 and 5,492,840).

Biosensors are of particular use in high throughput analysis due to the ease of adapting such systems to micro- or nanoscales. Furthermore, such systems are conveniently adapted to incorporate several detection reagents, allowing for multiplexing of diagnostic reagents in a single biosensor unit. This permits the simultaneous detection of several proteins or peptides in a small amount of body fluid.

The data presented herein clearly show that a cleaved caspase-3 product, the caspase-3 p17 fragment, is detectable in human circulation. The caspase-3 p17 level is increased by 50-100 percent in patients in the acute myocardial infarction phase. Thus, the level of caspase-3 proteolytic fragment can be used as a novel marker for myocardial infarction, whether STEMI or NSTEMI.

The disclosure is further illustrated by the following non-limiting examples.

EXAMPLES

Methods

Identification of Patients: The study population consisted of 27 consecutive patients admitted for primary PCI for acute ST Elevation Myocardial Infarction (STEMI) from December 2007 to January 2010 at the University of Connecticut Health Center. All patients underwent primary percutaneous coronary intervention upon admission and received subsequent clinical care in a standard manner. STEMI was defined as ST segment elevation mV in unipolar leads or mV in the anterior leads with a cTnI above 0.05 µg/1 associated with a rise or fall during subsequent sampling. cTnI, creatine kinase (CK) and CK-MB were measured at admission and then every 8 hours for 24-36 hours. Peak levels were ascertained retrospectively from the serial samples and were determined as the highest level if there was at least 1 lower value before and after the peak value. Informed consent was obtained from all subjects with a protocol that was approved by Institutional Review Board at the University of Connecticut Health Center.

A total of 27 patients were included. All had occluded infarct-related artery with TIMI 0 or 1 grade flow. Primary percutaneous coronary intervention (PCI) was performed with successful reperfusion in all subjects. Post-PCI Thrombolysis In Myocardial Infarction (TIMI) flow was grade 3 in 89% of patients and grade 2 for the remaining patients. There were no complications such as stroke, renal failure, shock or need for coronary artery bypass surgery. Baseline clinical characteristics of the study population are shown in Table 1.

TABLE 1

| Baseline Characteristics of STEMI Subjects | |
|---|---|
| Risk Factors: | Number (%) |
| Family History | 5 (19) |
| Diabetes | 4 (15) |
| Age | 56.9 ± 10.6 |
| Gender male/female | 25(93)/2(7) |
| Tobacco Current/Former | 11 (41)/5 (19) |
| History of Prior MI | 8 (30) |
| Hypertension | 15 (56) |
| Hyperlipoproteinemia | 12 (44) |

TABLE 1-continued

Baseline Characteristics of STEMI Subjects

| Risk Factors: | Number (%) |
|---|---|
| History of A Fib | 1 (4) |
| History of PVD | 0 |
| History of CVA/TIA | 1 (4) |
| Reestablished TIMI-3 flow | 24 (89) |
| LVEF | 52.8 ± 8.5 |

Data were means and standard deviations for a total of 27 STEMI subjects.
A Fib = atrial fibrillation;
PVD = peripheral vascular disease;
CVA = cerebrovascular accident;
TIA = transient ischemic attack;
LVEF = left ventricular ejection fraction;
TIMI-Thrombolysis In Myocardial Infarction.

Caspase-3 p17 and MI biomarker measurements: Caspases are a family of cysteine acid proteases that are essential to the apoptotic cascade. Pro-apoptotic signals trigger the activation of initiator caspases (such as caspase-8, -9, -10), which cleave and in turn activate effector caspases. Among the effector caspases, caspase-3 is considered to be the end executioner in the apoptotic pathway. It is activated by cleavage of its inactive zymogen into active p17 and p12 fragments. The cleaved p17 fragment in serum was directly detected with a commercial sandwich ELISA assay (PathScan™ Cleaved Caspase-3 (Asp175) Sandwich ELISA Kit from Cell Signaling Technology) as follows. Subjects underwent venipuncture to obtain a single gold-top tube of blood. Samples were centrifuged for 10 minutes at 4° C. and serum stored at −80° C. until assay. Serum was diluted 1:1 in sample diluent buffer, incubated at 42° C. for 15 min, plated on a 96-well microplate coated with caspase-3 antibody, which binds both full length caspase-3 and the p17 fragment. The incubation at 42° C. for 15 min resulted in less variability amongst triplicate determinations. After incubation overnight at 4° C., the microplate was washed with buffer, and incubated with cleaved caspase-3 (Asp175) antibody for 60 minutes at 37° C. This antibody recognizes only the cleaved p17 fragment of caspase-3. Samples were then incubated with a horseradish peroxidase (HRP)-linked secondary antibody for 30 minutes at 37° C., followed by reaction with the chromogenic substrate 3,3',5,5'-tetramethylbenzidine (TMB) at 25° C. for 20 min. The amount of p17 was determined by spectrophotometric analysis at 450 nm ($OD_{450}$) using a Multi-Detection Microplate Reader (Biotek, Model Synergy 2, Winooski, Vt.). Negative controls in which phosphate buffered saline (pH=7.4) was mixed with diluent buffer, were used to define the blank value for the assay and resulted in 0.05±0.01 $OD_{450}$ unit. For positive controls, apoptosis of HeLa cells (90% confluent) was induced by exposure to staurosporine (1 µM) for three hours at 37° C. as previously described (19). HeLa cells (American Type Culture Collection, Manassas, Va.) were cultured in Eagle's Minimum Essential Medium or MEM (Gibco Products, Invitrogen Corp, Grand Island, N.Y.) in the presence of 2 mM L-glutamine and 10% Fetal Bovine Serum (FBS) at 37° C. and 5% CO2-95% air. After 2 passages, cells were grown in 6-well plates till 90% confluence under identical culturing conditions. Cells were then incubated in the same MEM medium without serum for 16 hrs. MEM was replaced by phosphate-buffered isotonic saline (PBS, pH=7.4) before staurosporine was added. Lysates were run at various concentrations using identical conditions.

In another experiment, it was tested whether apoptotic HeLa cells can release p17 peptide into the medium in which the cells are incubated. HeLa cells were incubated in the presence of varying amounts of PBS (pH=7.4) containing 1 µM staurosporine for 3 hrs. The amount of p17 peptide in both the medium and cell lysates was assayed using the ELISA. The ratio of p17 in the medium to the total p17 peptide (medium p17 plus cell lysate p17) was plotted as a function of the amount of the medium bathing the apoptotic cells.

The p17 levels were measured at least twice 8-hours apart during the initial 24 hours after admissions and were considered the acute MI values. A subsequent determination was made 88±29.3 days (±SE) after the acute MI and is considered the post-MI value. The peak level was assumed to occur within 24 hours after reperfusion and was determined as the higher of the two acute MI values and was uniformly higher than the post-MI value.

CTnI was determined by the Access AccuTnI assay as is known in the art. CK-MB was determined by the Access CK-MB assay and both cTnI and CK-MB (µg/L) levels were measured using Beckman DXI 800. The 99$^{th}$ percentile value was used as the upper reference limit.

Cardiac Catheterization and Echocardiography: LV ejection fraction (LVEF) was obtained by visual inspection from echocardiography within 24 hours of admission to the hospital. Percutaneous coronary intervention was performed with a door-to-balloon time of less than 90 minutes.

Statistical Analyses: Means and standard errors for normally distributed variables or medians with interquartile ranges for non-normally distributed variables were used to describe continuous variables. Given that cTnI, CK, CK-MB and p17 values are not normally distributed, correlations were calculated using Spearman rank correlation. The non-parametric Wilcoxon Signed Rank test was used for paired comparisons between peak acute MI p17 and post-MI values. For analysis of difference between peak acute MI p17 value or post-MI p17 value and p17 value of healthy control subjects, Mann-Whitney test was used. For all analyses, a P value of less than 0.05 was considered significant. All P values reported were two-sided. Statistical analyses were performed with SPSS version 15.0 (SPSS Inc, Chicago, Ill.).

Example 1

Caspase-3 p17 Peptide in Apoptotic HeLa Cells

Figure 1:
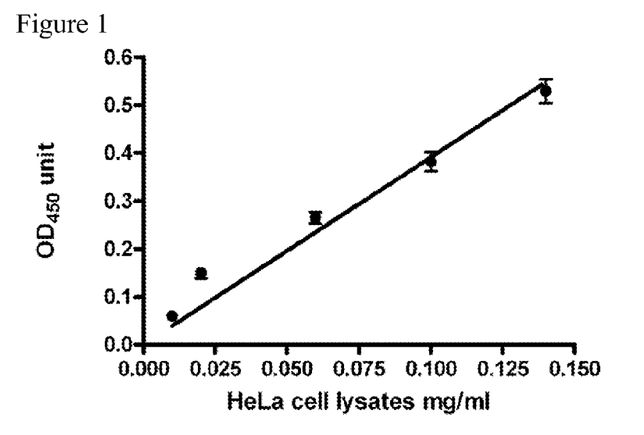
FIG. 1 shows the linearity of apoptotic HeLa cell lysates with P17 peptide level. Human HeLa cells were induced into apoptosis by prior treatment with staurosporine (1 μM) for three hours at 37° C. $OD_{450}$ represented the amount of p17 peptide.
Figure 2:
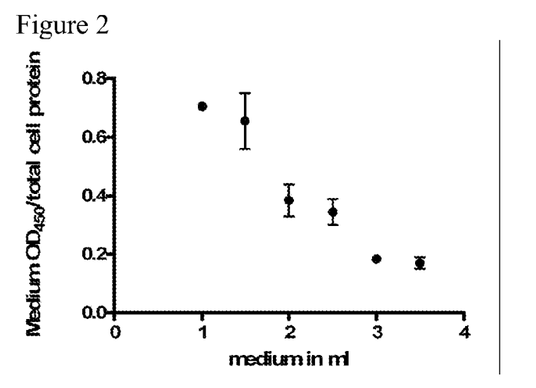
FIGS. 2 and 3 show that apoptotic HeLa cells release p17 peptide into the extracellular medium. HeLa cells were grown to 90% confluence and then subjected to varying amounts of staurosporine-containing PBS to induce apoptosis. After 3 hours, the amount of p17 peptide in 50 μl of the PBS medium was measured as $OD_{450}$ and normalized to the total amount of HeLa cell proteins (FIG. 2) or to the total combined amount of lysate plus medium $OD_{450}$ (FIG. 3). The data were then plotted as a function of the amount of medium. Total combined $OD_{450}$ was the total p17 peptide formed as a result of staurosporine treatment.
Figure 3:
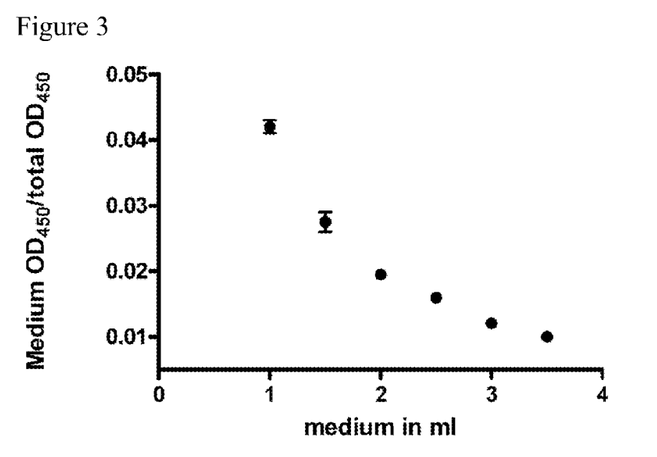

The p17 levels were linearly related to the amount of cell lysates obtained from HeLa cells treated with staurosporine (FIG. 1), which was known to cause apoptosis. To test whether the cleaved caspase-3 p17 peptide can escape the apoptotic cells and become detectable in extracellular medium, apoptosis of HeLa cells was induced and the presence of p17 peptide in medium bathing the apoptotic cells was investigated. Data summarized in FIGS. 2 and 3 showed that p17 peptide was easily detectable in medium. Its concentration in the medium was diluted progressively with increasing amounts of the medium in which apoptotic cells were incubated.

In relating the assay for p17 peptide to the serum quantitation of this peptide in humans, serum p17 $OD_{450}$ was in the linear range of the curve. The intra-subject or intra-class correlation coefficient in a group of 50 healthy control subjects repeated on 2 consecutive days was 0.61, P<0.01, (0.0417±0.014, mean and SD) to another (0.040±0.013).

Example 2

Serum Caspase-3 p17 Levels in AMI

Figure 4:
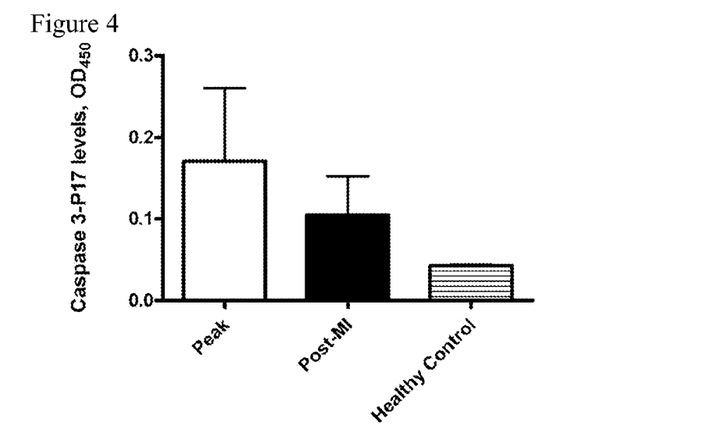
FIG. 4 shows caspase-3 p17 peptide levels during and after acute STEMI. Serum samples were obtained from patients with STEMI and from healthy subjects and p17 peptide levels measured. The peak level (n=27) during the acute event, the post-MI level (n=21), and the level from healthy subjects (n=167) were presented as means and SE. P<0.05 peak vs. post-MI, Wilcoxon Signed Rank test; P<0.05 healthy vs. peak or post-MI, Mann-Whitney test.
Figure 5:
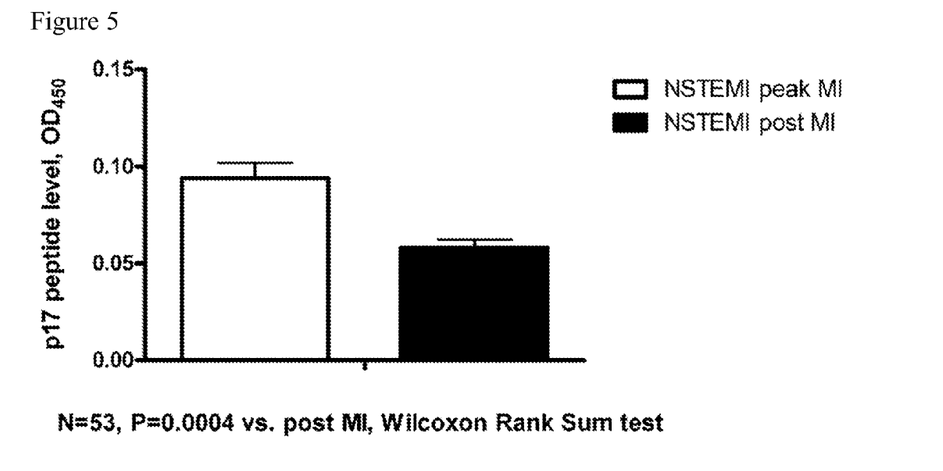
FIG. 5 shows serum p17 level is elevated during NSTEMI. Fifty three patients with NSTEMI, excluding those with acute heart failure, were enrolled. Serum caspase-3 p17 level was measured.

The peak serum p17 peptide level during acute MI was higher than the post-MI serum level in 21 subjects in whom samples were available during both phases (0.171±0.090 OD unit vs. 0.105±0.048 OD unit respectively, mean±SE, P=0.0016). Serum samples displaying peak value were obtained 23.0±13.3 hr (mean and SD) after admission. Compared to healthy subjects without evidence or history of heart disease, the peak acute MI p17 level (median of 0.080 with an interquartile range from 0.050 to 0.091) was nearly 4 fold higher than that in sera of healthy subjects (median of 0.041 with an interquartile range of 0.034 to 0.050, n=167 subjects, Mann-Whitney test, P<0.0001) (FIG. 4). The post-MI p17 peptide level (median of 0.052 with IQ=0.034 to 0.073) was also higher than that of healthy subjects (P=0.016, FIG. 3).

Example 3

Correlations with Biomarkers for Acute MI

In all subjects, the peak p17 peptide level occurred after PCI. Similarly, the peak cTnI, CK, and CK-MB values were obtained within 24 hours after reperfusion. Data summarized in Table 2 showed that peak p17 peptide level was positively correlated with the peak cTnI and peak CK-MB levels. After $\log_{10}$ transformation, peak p17 peptide and CK-MB values remain non-normally distributed (D'Agostino and Pearson omnibus normality test). The $\log_{10}$ transformed peak p17 peptide values remained positively correlated with $\log_{10}$ transformed peak cTnI (r=0.48, P=0.011, Spearman) and $\log_{10}$ transformed peak CK-MB (r=0.56, P=0.002, Spearman).

TABLE 2

Correlation of Peak Caspase-3 p17 Peptide Level with Peak Troponin and Peak CK-MB

|  | P17 peptide OD$_{450}$ | cTnI µg/L | CK-MB µg/L |
| --- | --- | --- | --- |
| Peak Serum Level Correlation | 0.171 ± 0.090 | 34.16 ± 5.24 | 148.4 ± 21.1 |
| Spearman r | — | 0.48 | 0.56 |
| 95% CI | — | 0.109 to 0.732 | 0.226 to 0.783 |
| P value (2-tailed) | — | 0.011 | 0.002 |

Peak circulating p17 peptide level was measured and was positively correlated with peak cTnI and CK-MB levels during acute STEMI in 27 patients.

Example 4

Serum p17 Level is Elevated During NSTEMI

Fifty three patients with NSTEMI, excluding those with acute heart failure, were enrolled after informed consent, which was approved by the Institutional Review Board at University of Connecticut Health Center. Serum caspase-3 p17 level was measured as described in Methods. Data were means and SE. Peak p17 level during acute NSTEMI (termed peak MI) is higher than that obtained after recovery from acute MI (termed post MI), P=0.0004, Wilcoxon Rank Sum test. In addition, both the peak and post MI levels are higher than that of a group of control healthy volunteers (P<0.0001).

Together these studies have demonstrated for the first time elevated serum caspase-3 p17 peptide levels during the acute phase of STEMI and NSTEMI, supporting the presence of acute, probably myocardial apoptosis in humans. If myocardial apoptosis is a major contributor to the injury that occurs during AMI, then designing therapies to inhibit it may provide benefit to both STEMI and NTEMI patients.

The terms "a" and "an" herein do not denote a limitation of quantity, but rather denote the presence of at least one of the referenced item.

All ranges disclosed herein are inclusive and combinable. While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A prognostic method for determining a likelihood of a future myocardial infarction in an individual diagnosed as having had a myocardial infarction, comprising directly or indirectly measuring a peak acute myocardial infarction level of a caspase-3 proteolytic fragment in a blood sample taken from the individual during the acute phase of myocardial infarction, wherein the caspase-3 proteolytic fragment is the p17 or the p12 fragment, directly or indirectly measuring a post-myocardial infarction level of the caspase-3 proteolytic fragment in a blood sample taken at least one week post-myocardial infarction, comparing the peak acute myocardial infarction level and the post-myocardial infarction level of the caspase-3 proteolytic fragment to a control level of the caspase-3 proteolytic fragment, and predicting the likelihood of future myocardial infarction, left ventricular dysfunction, death in the individual diagnosed as having had a myocardial infarction when an elevated peak acute myocardial infarction level compared to the control level of the caspase-3 proteolytic fragment and an elevated post-myocardial infarction level compared to the control level of the caspase-3 proteolytic fragment are observed, and the elevated peak acute myocardial infarction level compared to the control level of the caspase-3 proteolytic fragment is higher than the elevated post-myocardial infarction level compared to the control level of the caspase-3 proteolytic fragment, wherein an elevated peak acute myocardial infarction level of the caspase-3 proteolytic fragment is at least 30% greater than the control level of the caspase-3 proteolytic fragment.

2. The method of claim 1, wherein the individual has been admitted to an emergency room for a suspected myocardial infarction.

3. The method of claim 2, the individual has been admitted to the emergency room for primary percutaneous coronary intervention.

4. The method of claim 1, wherein at least one blood sample is taken after the administration of reperfusion therapy to the individual.

5. The method of claim 1, wherein the myocardial infarction is ST elevation myocardial infarction or non-ST elevation myocardial infarction.

6. The method of claim 1, wherein detecting is by immunoassay with an antibody specific for the caspase-3 p17 or p12 fragment.

7. The method of claim 1, wherein detecting is by mass spectrometry.

* * * * *